United States Patent [19]

Broz et al.

[11] Patent Number: 4,787,952
[45] Date of Patent: Nov. 29, 1988

[54] TEMPERATURE MODULATED GLUE BEAD TESTING APPARATUS

[75] Inventors: Curtis H. Broz, Roseville, Minn.; Eugene A. Koll, Moundsview; Theodore Peltier, Hugo, both of Minn.

[73] Assignee: Champion International Corporation, Stamford, Conn.

[21] Appl. No.: 717,001

[22] Filed: Mar. 28, 1985

[51] Int. Cl.$^4$ ................................................ B29F 3/08
[52] U.S. Cl. ................................ 156/359; 73/150 A; 118/667
[58] Field of Search .................. 156/378, 64, 359; 73/150 R, 150 A; 425/141, 144; 118/667

[56] References Cited

U.S. PATENT DOCUMENTS

| | | | |
|---|---|---|---|
| T916,005 | 11/1973 | Dolen et al. | 73/150 A |
| 2,898,816 | 8/1959 | Keely | 156/357 X |
| 3,444,732 | 5/1969 | Robbins et al. | 156/378 X |
| 3,490,278 | 1/1970 | Van Saun et al. | 73/150 A |
| 3,743,562 | 7/1973 | Phipps | 156/378 |
| 4,454,084 | 6/1984 | Smith et al. | 425/144 X |

Primary Examiner—David Simmons
Attorney, Agent, or Firm—Evelyn M. Sommer

[57] ABSTRACT

A testing apparatus is provided for applying a glue bead to a first sheet of material and then adhering a second sheet of material thereto. The testing apparatus includes a glue tank and a glue head attached thereto both of which are adapted to measure and control the temperature of the glue therein. The glue head applies the glue to the first sheet of material at a preselected rate. The first sheet of material then passes to a compression cylinder which urges the second sheet of material into contact with the first sheet of material. The pressure and duration of the contact between the first and second sheets of material can be varied.

17 Claims, 3 Drawing Sheets

TEMPERATURE MODULATED GLUE BEAD TESTING APPARATUS

BACKGROUND OF THE INVENTION

Paper or paperboard structures often include a plurality of sheets of material adhered in face-to-face contact. For example, most envelopes, cartons, display structures, and the like include seams or reinforced areas where at least portions of adjacent sheets of paper or paperboard material are adhered together.

The required strength of the adhesive bond between adjacent sheets of paper or paperboard is dependent upon the intended end use of the completed structure. This bond strength is affected by many factors including: the respective characteristics of the paper or paperboard being adhered; the type of adhesive; the rate of application of adhesive; the temperature of the adhesive at the instant of application; the pattern by which the adhesive is applied; the elapsed time between the application of the adhesive to the first sheet and the contact of the second sheet thereto; and the amount and duration of pressure applied in securing the two sheets together.

The many factors that affect adhesive bonds make it difficult to precisely determine the specific parameters for adhering sheets of paperboard to one another. The determination of specific adhesion characteristics is particularly difficult in view of the infinite number of possible bond strength requirements, and the ever-changing availability of adhesives on the market. Consequently it is necessary for the manufacturer of paperboard structures to undertake a significant amount of testing to determine the proper bonding parameters.

Automatic testing equipment is available for experimenting with and determining the proper adhesive application and bonding parameters. For example, one such piece of testing equipment is shown in U.S. Pat. No. 3,490,278 which issued to Van Saun et al on Jan. 20, 1970. The apparatus shown in U.S. Pat. No. 3,490,278 is directed to a machine including a chain and a pusher for advancing a sheet of paper or paperboard material in a longitudinal direction along a test path. A hot melt adhesive applicator is disposed in the test path of the prior art machine. The applicator is connected by conventional means to a hot melt adhesive auxiliary unit. This auxiliary unit on the prior art test machine is spaced from the applicator and includes controls that can be used to adjust the temperature of the adhesive in the auxiliary unit and to vary the rate of flow of adhesive from the auxiliary unit. Thus, the testing machine shown in U.S. Pat. No. 3,490,278 provides a crude apparatus for controlling the temperature and flow rate of adhesive to an adhesive applicator spaced therefrom. The machine of U.S. Pat. No. 3,490,278 further includes a pressure mechanism for holding a second sheet of material by vacuum. An appropriate external signal will cause the pressure elements to advance toward one another, thereby placing the two sheets into face-to-face contact with the adhesive disposed therebetween. The amount of pressure and the duration of pressure application can be externally varied.

The machine of U.S. Pat. No. 3,490,278 has several significant deficiencies. Specifically, it is now known that the precise temperature at which a hot melt adhesive is applied can significantly affect the bonding characteristics. However, the machine of U.S. Pat. No. 3,490,278 only attempts to control the hot melt adhesive temperature in an auxiliary unit that is spaced from the actual applicator of adhesive. In travelling to the actual applicator, the hot melt adhesive temperature can vary significantly, thereby affecting the quality of the adhesive bond. Additionally, glue disposed adjacent the nozzle can cool substantially between adjacent tests. Since the test bead is usually quite short, a large part of each test bead can be much cooler than the heated glue in the auxiliary unit. Another deficiency of the machine shown in U.S. Pat. No. 3,490,278 is the inclusion of a large number of manually controllable externally initiated operations. Consequently there is a substantial probability of significant variations from one test to the next, thereby giving inaccurate or misleading test results.

Another testing machine is shown in U.S. Pat. No. 3,444,732 which issued Robbins et al on May 20, 1969. The testing apparatus shown in U.S. Pat. No. 3,444,732 addresses the importance of temperature control, but only is concerned with that part of a manufacturing process where heat and pressure are applied to a preexisting bead of glue. U.S. Pat. No. 3,444,732 does not address the step-by-step analysis and testing of other factors involved in the manufacture of paper or paperboard structures, and further is not concerned with the accurate testing and control of conditions related to the application of adhesives.

In view of the above, it is an object of the subject invention to provide an apparatus for testing the various parameters that are essential to accurate adhesive bonding during the manufacture of paper or paperboard products.

It is another object of the subject invention to provide an apparatus for automatically and reliably testing the rate and temperature of adhesive as it is being applied to a sheet of paper or paperboard material.

It is an additional object of the subject invention to provide an apparatus for accurately testing and controlling adhesive application and subsequently testing and controlling the amount and duration of pressure between two sheets of material being adhered to one another.

It is a further object of the subject invention to provide an apparatus capable of automatically and reliably repeating or varying a plurality of testing parameters.

It is still another object of the subject invention to provide an apparatus that will ensure that glue temperature will remain constant throughout each test and can be controlled from one test to the next.

SUMMARY OF THE INVENTION

The testing apparatus of the subject invention includes a housing having a generally planar top surface. The top surface is provided with an elongated generally linear slot through which one or more pushers extend for advancing the lower sheet of paper or paperboard material. Guides extending parallel to the slot in the housing may be provided on the top surface to define a test path that carefully controls the longitudinal movement of the bottom sheet of material. Preferably at least one of the guides is adjustable in the lateral direction to accomodate lower sheets of various dimensions.

Each pusher is mounted to a means for moving the pusher along the entire length of the slot. Preferably, each pusher is mounted to a flexible closed loop, such as a belt or chain, at least a portion of which extends parallel to and adjacent the slot. The closed flexible loop to which the pusher is mounted is in communication with a motor adapted to move the loop and the pushers attached thereto. Preferably the motor is a variable speed motor that will enable the rate of speed of the pushers travelling through the slot to be adjusted according to preselected parameters.

A glue applicator means is spaced from the top surface of the housing, and is substantially in line with at least a portion of the test path. Thus, the pusher will advance the bottom sheet of material between the glue applicator means and the top surface of the housing.

Preferably, the glue applicator means includes a glue tank means and a glue head means. Preferably, the tank means is in communication with a source of pressure and an adjustment means for selectively controlling the amount of pressure directed into the glue tank means. The pressure from the source of pressure is operative to urge the glue from the glue tank means and to the glue head means as explained below. The rate of flow of glue from the glue tank means to the glue head means can be carefully controlled and monitored by adjusting the level of pressure directed into the glue tank means. In the preferred embodiment, this pressure in the glue tank means can be measured and controlled through control means incorporated into the housing.

The glue tank means also is in communication with a temperature probe and a heat source. The temperature probe, such as a thermometer means and/or thermostat means is adapted to precisely measure the temperature of the adhesive in the glue tank means. The heat source is operative to selectively raise the temperature of the glue in the glue tank means. Preferably the heat source is entirely electrical, with temperature varying as a function of resistance and/or current flow. The means provided for measuring and controlling the temperature preferably is mounted in the housing and is in communication with an easily readable temperature gauge and adjustment means mounted in a prominent position on the housing.

The glue head means includes a glue nozzle through which the glue is advanced for application to the bottom sheet of material. Preferably the nozzle of the glue head means is replaceable and/or adjustable. Thus, the nozzle can be used to selectively vary the amount and pattern of glue being applied to the bottom sheet of material. The glue head means also is provided with means for measuring and controlling the temperature and pressure of the glue passing therethrough. As explained above, these means can include a temperature probe, such as a thermometer and/or thermostat and a heat source for selectively varying the temperature of glue disposed in and passing through the glue head. The means for measuring and controlling the temperature and pressure of glue in the glue head also is observable and controlled through the housing as explained with respect to the temperature controls for the glue tank.

The separate temperature and pressure controls for the glue tank means and glue head means achieve several significant objectives. First, the temperature is assured of being at the selected level as it is being applied to the bottom sheet of material, rather than as it is leaving the glue tank. Second, the problem of glue in the glue head cooling between successive tests is avoided. Thus, the glue temperature will be uniform between successive tests and throughout each individual test. Third, the separate pressure means in the glue tank and glue head more positively control the rate of the flow of glue.

Preferably, the glue tank is pivotally mounted to the housing. Thus, the glue tank means can readily be rotated away from the housing when glue is to be poured into the tank or when the tank is to be cleaned. This prevents glue from being inadvertently spilled onto the housing and in particular the moving parts attached thereto. Furthermore, this unique construction minimizes the space requirements of the apparatus and prevents the need for a separate glue tank auxiliary unit that otherwise might be required.

Preferably, the glue head and/or glue tank are in communication with a trip switch incorporated into the housing adjacent the slot therein. The trip switch is disposed such that glue will automatically be dispensed from the glue head means when the bottom sheet of material is properly positioned relative to the glue head means.

The apparatus further includes a compression means for controlling the top sheet of material. Preferably, this means comprises a compression bar in communication with a vacuum source. The vacuum source is sufficient to hold the top sheet of material against the compression bar. Preferably this vacuum source is adjustable, thereby enabling different sizes and weights of material to be tested for the top sheet.

The compression bar is mounted to a means for moving the compression bar toward the top surface of the housing. Preferably this latter means is a hydraulic or pneumatic piston which operates under pressure to advance the compression bar toward the top surface of the housing. It also is preferred that this means be adjustable both in terms of the amount and duration of the pressure application. In operation, this part of the apparatus would first hold the top sheet of material to the compression bar and then advance the top sheet of material into face-to-face contact with the bottom sheet of material. It is preferred that the controls for both the amount and duration of this pressure in the piston be mounted in the housing.

The apparatus of the subject invention is used by first activating the vacuum in the means for controlling the top sheet of material. The top sheet then is positioned adjacent the compression bar and is held in that position by the vacuum. The bottom sheet of material then is placed in the path defined on the top surface of the housing. The lateral dimension of the path can be adjusted at this point to insure that the bottom sheet advances along the intended path. The desired speed for the movement of the chain then is selected. The pressure and temperature of the glue and the particular nozzle type and setting also is selected and set at this time.

After the preselection of the various variables that will affect the application of glue onto the bottom sheet of material, the means for moving the pusher is activated thereby causing the pusher to contact the bottom sheet of material and advance the bottom sheet of material along the path defined on the top surface of the housing. When the bottom sheet of material is in line with the glue head means, the bottom sheet will contact and activate the trip switch thereby causing the pressure to be directed into the glue tank means and glue head means, and thus causing the flow of glue through the nozzle. As the bottom sheet of material advances further, a second trip switch will be contacted and activated causing the pressure into the glue tank means and glue head means to be terminated and thereby stopping the flow of glue.

The bottom sheet of material then will advance into position underneath the top sheet of material. At this point, movement of the bottom sheet will be stopped and the top sheet will be advanced into contact with the bottom sheet. The amount and duration of pressure between the top and bottom sheets is precisely controlled in accordance with the preselected parameters. After the selected duration of time has elapsed, the compression bar will be withdrawn allowing the adhered first and second sheets of material to be removed and analyzed.

The preferred construction of the apparatus will be explained and illustrated in greater detail below. However, it should be noted that the various controls and gauges should be located in close proximity to one another to enable accurate and easy analysis and control of the various variables.

DETAILED DESCRIPTION OF THE PREFERRED EMBODIMENT

Figure 1:
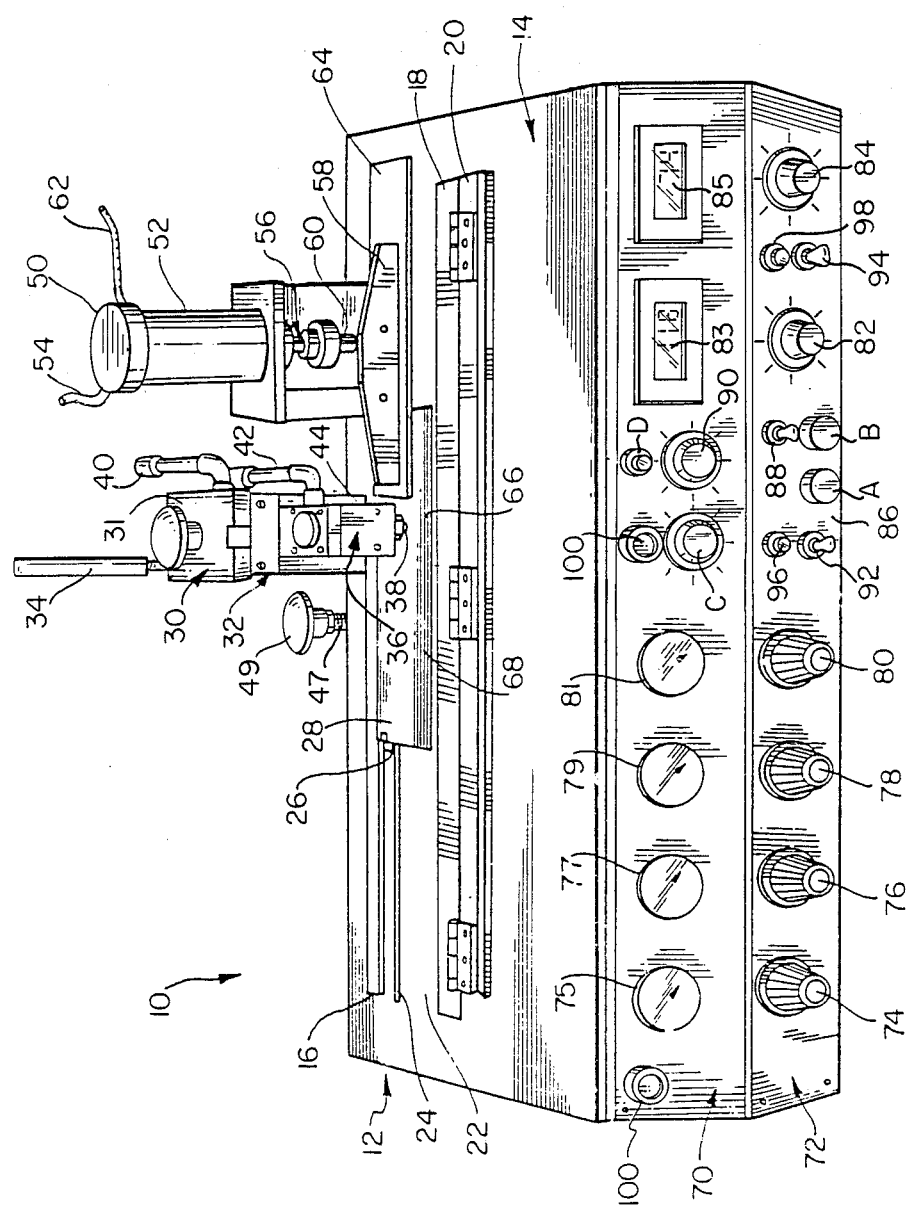
FIG. 1 is a perspective view of the apparatus of the subject invention.

The apparatus of the subject invention is indicated generally by the numeral 10 in FIG. 1. The apparatus 10 includes a generally rectangular housing 12 having a planar top surface 14. The top surface 14 includes an elongated guide 16 fixedly attached to the top surface 14. An adjustable guide 18 also is mounted to the top surface 14 and is parallel to the fixedly mounted guide 16. The adjustable guide 18 can be moved toward or away from the fixedly mounted guide 16. The adjustable guide 18 further includes a hingedly attached cover portion 20 which can be rotated toward the fixedly attached guide 16 to prevent a piece of paper or paperboard material placed therebetween from flying upwardly away from the top surface 14. The portion of the top surface 14 intermediate the guides 16 and 18 defines a test path 22 through which a sheet of material may pass. The guides 16 and 18 insure that the sheet of material will travel substantially linearly.

The top surface 14 is provided with a longitudinally extending slot 24 disposed in test path 22 and extending substantially parallel to the guides 16 and 18. As explained further below, at least one pusher 26 is mounted internal to housing 12 but extending through slot 24. The pusher 26 is moveable along the length of slot 24 and is adapted to push a bottom sheet of paperboard material 28 along path 22.

Figures 2, 4:
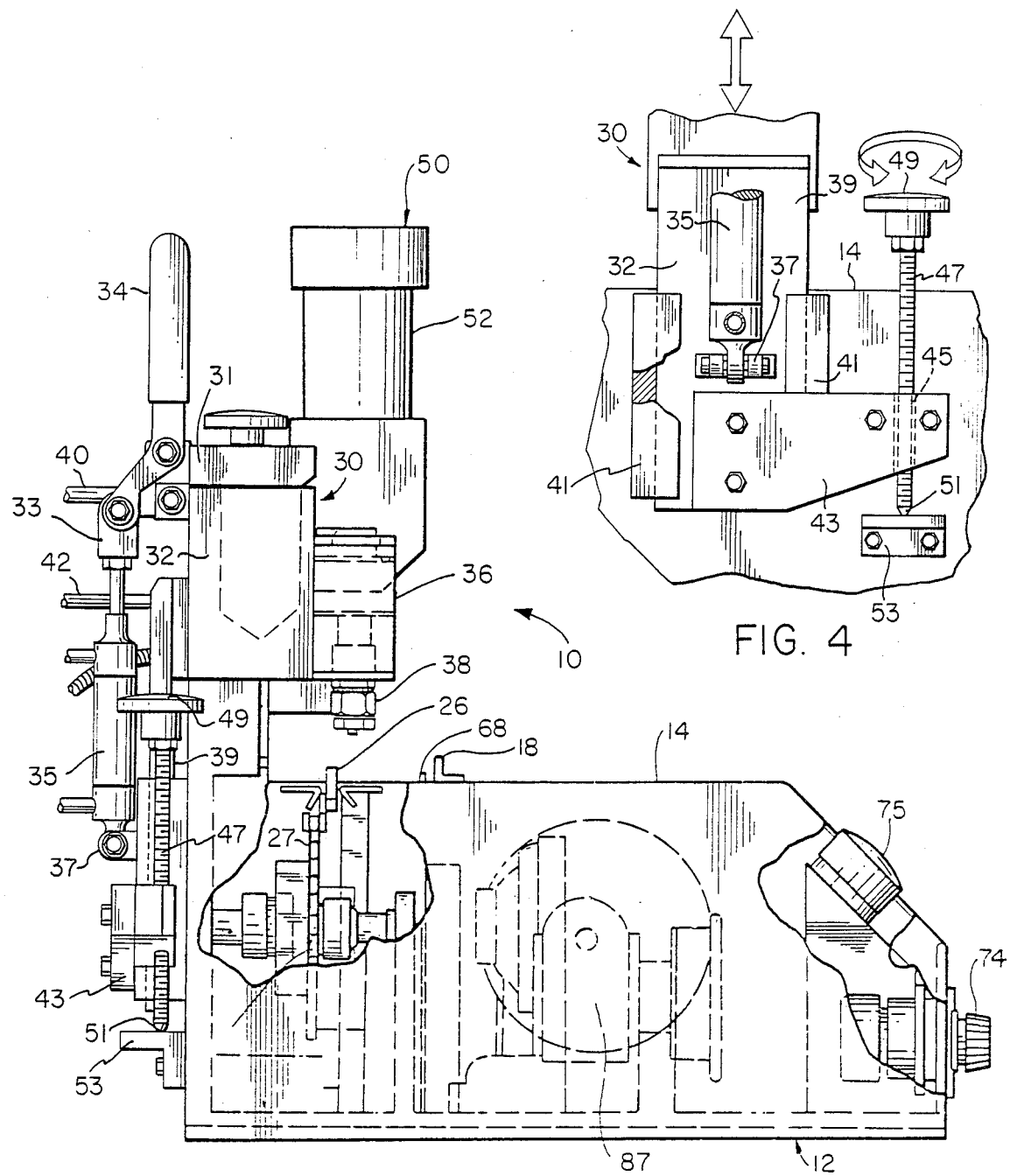
FIG. 2 is a side elevational view partially broken away of the apparatus of the subject invention, as seen from the left hand side of FIG. 1.
FIG. 4 is a rear elevational view, partially broken away and in section, of the glue tank of the apparatus of the present invention mounted on the rear of the apparatus.

A glue applicator assembly 30 is adjustably mounted in spaced relationship to the top surface 14 of housing 12. The glue applicator assembly 30 comprises a glue tank 32 provided with a cover 31 that can be opened by rotating a handle 34 rotatably fixed to cover 31 and rotatably mounted on a bracket 33 connected to the extensible piston of a fluid cylinder 35, which in turn is pivotably mounted on a bracket 37 on the rear of a plate 39. Plate 39 is fixed to the rear of glue tank 32 and slidably received between a pair of L-shaped guides 41 mounted on the rear of housing 12. A bracket 43 extends from one side of plate 39 and has a threaded bore 45 therethrough threadedly receiving an elongated screw 47 provided with a handle or knob 49 at one end for rotating screw 47 and a point 51 at its opposite end which is seated on a horizontal ledge of an L-shaped bracket 53. The glue tank 32 can be selectively raised or lowered by rotation of screw 47 which causes bracket 43 and plate 39 to slide between guides 41 to vary the distance between the glue applicator assembly 30 and the top surface 14 of housing 12. Precise adjustments to the distance between glue applicator assembly 30 and housing 12 can thus be made in accordance with the thickness of the bottom sheet of material 28. Additionally, by extending the piston rod of cylinder 35, the cover 31 cannot be opened by grasping and rotating handle 34. Retraction of the piston will allow the handle 34 to be grasped and rotated rearwardly (counterclockwise as viewed in FIG. 2) to completely open the cover so the tank 32 can be filled. By virtue of this construction, the glue tank 32 cannot be opened during operation of the apparatus for safety reasons preventing spillage of glue. However, by completely unthreading screw 47 from bore 45, the entire glue applicator assembly can be removed from guides 41 for cleaning or service.

Attached to the glue tank 32 is the glue head 36. The glue head 36 is in direct communication with the glue tank 32 such that the glue placed therein can be urged from the glue tank 32 through the head 36 and onto the bottom sheet of material 28. The glue head 36 includes an adjustable and replaceable nozzle 38 through which glue can be directed onto the bottom sheet of material 28. By adjusting or replacing the nozzle 38, the pattern and rate of flow of glue can be varied. Air pressure tubes 40 and 42 extend into the tank 32 and the head 36 respectively. The air pressure tubes 40 and 42 are in communication with a source of air pressure and with the pressure control means of the apparatus as explained further below. Pressurized air directed through the air pressure tubes 40 and 42 urges glue in the glue applicator assembly 30 onto the bottom sheet of material 28. The rate of application of glue can be varied by varying the amount of pressure being directed into either or both of the air pressure tubes 40 and 42.

The glue applicator assembly 30 further includes a temperature control and measurement apparatus 44 which is operative to measure and control the temperature of glue in the glue head 36 adjacent to the nozzle 38 thereof. Preferably, the temperature measurement and control apparatus is operable through a range of approximately 0° F. to 400° F. As explained further below, the controls and indicators for the apparatus 44 are incorporated into the housing 12.

A second temperature measurement and control apparatus is incorporated into the glue tank 32. This second apparatus is operative to control and measure the temperature of the glue in the glue tank 32. As with the apparatus 44 in the glue head 36, the second temperature measurement and control apparatus is in communication with control and display instruments incorporated into the housing 12. The simultaneous use of the first and second temperature measurement and control apparatus disposed respectively in the glue head 36 and the glue tank 32 enables a precise control of the glue temperature throughout the glue applicator assembly 30 and up to the point of application of glue on the bottom sheet of material 28.

A compressor assembly 50 is mounted to the housing 12 and disposed substantially adjacent the test path 22 on top surface 14 thereof. The compression assembly 50 includes a compression cylinder 52 from which pressure tube 54 extends. The pressure tube 54 is in communication with a source of air pressure (not shown) and also is in communication with instrumentation provided in the housing 12 as explained further below. The compression cylinder 52 includes a piston 56 to which a compression bar 58 is mounted. The piston 56 and compression bar 58 are disposed substantially in line with the path 22 on top surface 14 of housing 12. The piston 56 is operative to move toward and away from the top surface 14 such that the compression bar 58 can be urged substantially into face-to-face contact with the top surface 14. The portion of piston 56 adjacent the compression bar 58 is of generally hollow tubular construction and defines a vacuum nozzle 60, and through vacuum tube 62 is in communication with a source of vacuum (not shown) such as a vacuum pump. The vacuum at the vacuum nozzle 60 of piston 56 is adjustable, and is capable of creating a suction of approximately 50 psi. This vacuum enables a top sheet of material 64 to be held by the vacuum adjacent to the compression bar 58.

Switch means 66 and 68 are mounted adjacent top surface 14 of housing 12. More particularly, the switch means 66 and 68 are disposed within test path 22, and are operative to be triggered by the movement of the bottom sheet 28 along path 22. Switch 66 is disposed in test path 22 and intermediate the glue applicator assembly 30 and the compression assembly 50. Switch 66 is operative to initiate the flow of pressurized air through tubes 40 and 42 and thus to urge glue from the glue applicator assembly 30 onto the lower sheet 28. Switch 68 also is disposed in test path 22, but is on the side of the glue applicator assembly 30 opposite compression assembly 50. The switch 68 is operative to terminate the flow of glue after the lower sheet 28 has passed beyond switch 68.

The housing 12 further includes the means for regulating and monitoring the speed of pushed 26, the pressure in both the glue tank 32 and the glue head 36, the strength of the vacuum and compression provided by the compression assembly 50 and the dwell time during which the compression bar 58 is in the downward position. As depicted most clearly in FIG. 1, the housing 12 of apparatus 10 includes front walls 70 and 72 on which the various controls are positioned. More particularly, adjustment dial 74 is provided to control the level of air pressure to the compression cylinder 52. Adjustment dial 74 may be a valve incorporated into the pneumatic system, or alternatively may be an electrically operated means in communication with a solenoid valve in lines 54. The actual level of pressure in compression cylinder 52 and acting on the compression bar 58 is indicated by the compression gauge 75.

The level of pressure directed to the glue head 38 and the glue pot 32 are controlled respectively by adjustment dials 76 and 78. The actual pressure measured in the glue head 36 and glue pot 32 is indicated on the pressure gauges 77 and 79 respectively. As explained previously the adjustment dials can be valves in direct communication with pressure lines 42 and 40 respectively, or the adjustment dials 76 and 78 can be electrical switch means in communication with solenoid valves that are part of pressure lines 42 and 40.

Vacuum adjustment dial 80 and vacuum gauge 81 are provided to control and indicate the amount of suction provided in the vacuum nozzle 60 of piston 56. Since the principal function of the suction is to hold the upper sheet of material 64 adjacent to the compression bar 58 prior to activation of piston 56, the level of suction would not be subject to change very frequently. Typically, this suction will be maintained at approximately 50 psi. However, the vacuum gauge 81 is useful for indicating whether the suction is operable. It also may be necessary to alter the suction level for particularly light or particularly heavy upper sheets of material 64.

Dial 84 is provided to adjust the temperature of the glue in tank 32, while gauge 85 provides a visual digital readout of the actual temperature level in the glue pot. As indicated above, the temperature measuring and control devices are electrically operable. These electrical operations incorporate the temperature adjustment dial 84 and temperature gauge 85 by standard technology.

Figure 3:
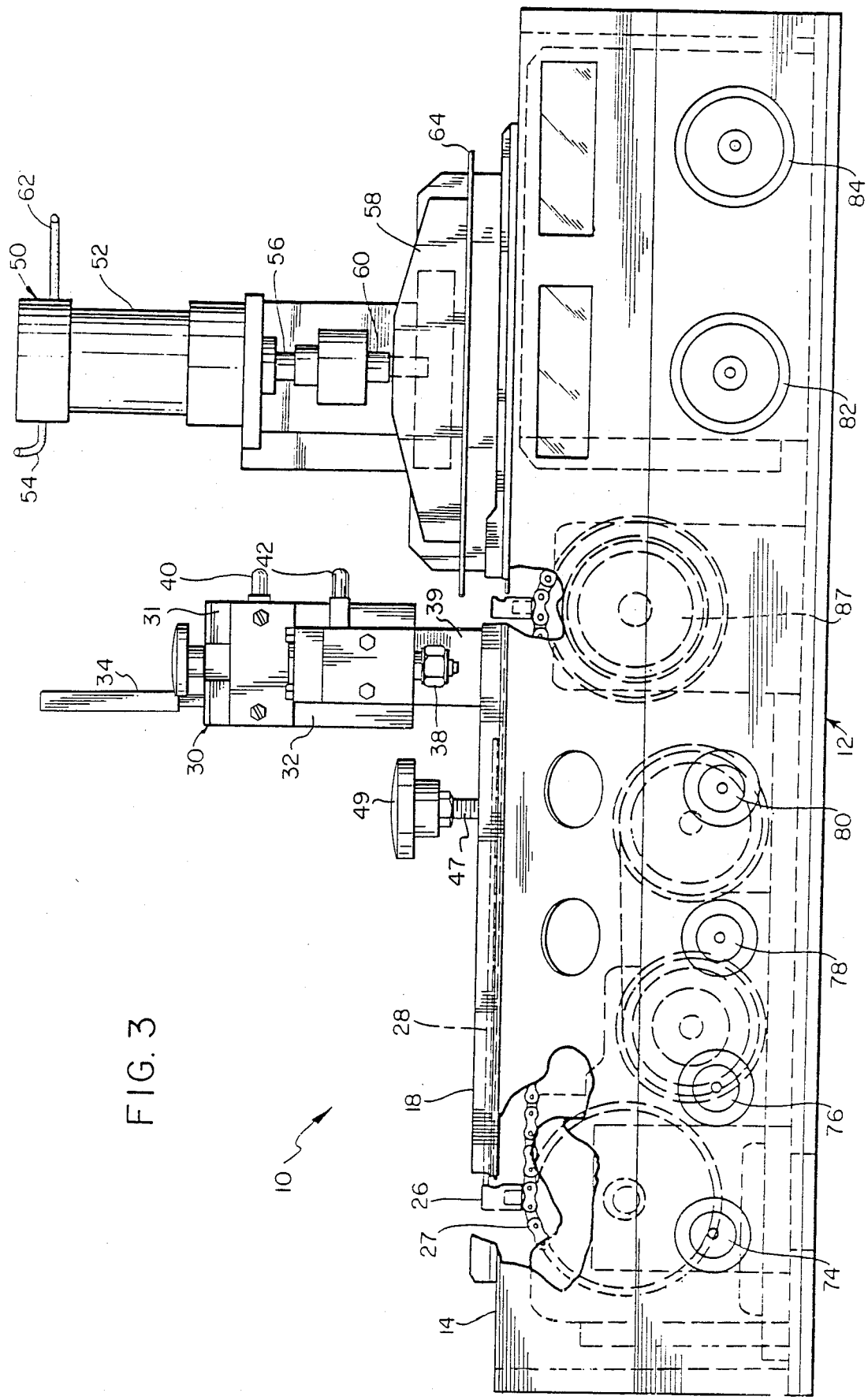
FIG. 3 is a front elevational view, partially broken away, of the apparatus of FIG. 1 of the subject invention.

The speed of pusher 26 is controlled by adjustment dial 82. Preferably, the speed is adjustable between 0 and 250 feet per minute. The adjustment dial 82 is in direct communication with the electrical motor 87 shown in FIGS. 2 and 3 which operate the chain or belt 27 to which the pusher 26 is attached. The motor switch 88 is in direct communication with the motor 87 for promptly starting or stopping the motor 87. A digital readout of the speed is indicated visually by gauge 83.

The dwell time of the compression bar 58 against the lower sheet 28 is controlled by dwell time dial 90. The dwell time dial 90 is in communication with a timing apparatus and a solenoid valve (not shown) for controlling the air pressure through pressure line 54 and into the compression cylinder 50. Thus, after completion of the selected dwell time the pressure in the compression cylinder 52 will be reversed causing the piston 56 thereof to be withdrawn.

The apparatus 10 further includes "power-on" switch 92 and glue switch 94. The power switch 92 controls the flow of power to the entire apparatus 10. The glue switch 94 initiates the heating of the glue in the glue tank. Indicators 96 and 98 are provided to show that the power switch 92 and the glue switch 98 are in the on condition.

Finally, a pair of cycle start switches 100 are provided which must be simultaneously activated to initiate the operation of the subject apparatus. Typically, the cycle start switches 100 will be started after the previously defined parameters have been selected and set. Other controls which may be incorporated in the apparatus 10 include a main power fuse A, a drive motor fuse B, a compression delay control switch C and a glue purge control switch D for initiating the cleaning of glue nozzle 38.

In operation, the various parameters to be tested are initially selected and set on the apparatus. Specifically, the glue nozzle 38 is selected and/or adjusted to provide the appropriate desired glue application pattern. The glue temperature level and application rates also are selected and set utilizing adjustment dials 76, 78, and 84. The rate of application of glue also will be determined by the speed at which the lower sheet 28 is moved relative to the glue apparatus 30. Therefore, speed adjustment means 82 is set to reflect the desired speed of movement of the lower sheet 28. The vacuum pressure utilized to hold the top sheet 64 against the compression bar 58 generally would not be changed. However, if the top sheet is of a particularly heavy or particularly light material the adjustment dial 80 may have to be varied accordingly. Finally, the level of pressure to be exerted by the compression bar 58 and the dwell time for the exertion of pressure by pressure bar 58 also must be selected and set with dials 74 and 90.

The testing procedure is initiated by first activating the power and glue switches 92 and 94. The lower sheet 28 then is placed in test path 22 adjacent to pusher 26 at a location along path 22 most distant from the glue apparatus 30 and pressure apparatus 50. The top sheet 64 then is positioned against the compression bar 58. The vacuum pressure through vacuum nozzle 60 will hold the top sheet 64 firmly against the compression bar 58 and spaced from the top surface 14.

At this point the entire testing procedure is set to begin. Therefore cycle start switches 100 may be activated causing the motor 87 to move the chain 27 and the pusher 26 attached thereto. The pusher 26 will slidingly advance the lower sheet 28 along path 22 at the preselected speed. The lower sheet 28 will contact and activate switch 66 causing the glue to be advanced through nozzle 38 and onto the lower sheet 28. The glue will continue to be applied until the lower sheet 28 clears switch 68, at which point the flow of glue through nozzle 38 will be terminated. As explained above, the starting and stopping of the flow of glue is controlled by pressure through lines 40 and 42. The lower sheet 28 will stop moving at a point approximately in line with the compression bar 58. At this time the compression cylinder 50 is activated causing piston 56 thereof to advance downwardly toward top surface 14. This action causes the top sheet 64 to be urged into contact with the bottom sheet 28. As the piston 56 reaches its maximum range of movement, the vaccum through vacuum nozzle 60 is terminated. The amount of pressure exerted by compression bar 58 and the duration of time through which this pressure is acting is in accordance with preselected and preset levels. After the dwell time has elapsed piston 56 will withdraw thereby terminating the pressure on the upper sheet 64. Other tests then can be performed utilizing the same parameters, or by altering the parameters as desired. The quality of the resulting bonds then can be evaluated to assess the best bond for use on the production line.

In summary, an apparatus is provided for accurately controlling and testing various parameters affecting the adhesion of sheets of paper or paperboard material to one another. The apparatus is capable of carefully controlling the rate of glue application, the temperature of glue, the pressure applied to the sheets being adhered and the duration of said pressure. The actual temperature of the glue being applied to the sheets is carefully monitored and controlled by temperature control means mounted both in the glue tank and in the nozzle. The glue apparatus is further specifically adapted to be easily rotated away from the apparatus to facilitate cleaning and refilling.

While the invention has been described with respect to a preferred embodiment, it is obvious that various changes and modifications thereto can be made without departing from the spirit of the subject invention which should be limited only by the scope of the appended claims.

What is claimed is:

1. A glue bead testing apparatus for applying a bead of glue to a first sheet of paper or paperboard material and adhering a second sheet of paper or paperboard material thereto, said apparatus comprising:
   a housing;
   guide means mounted to said housing and defining a test path;
   pusher means for moving the first sheet of material along the test path;
   glue tank means mounted to said housing for storing the glue;
   glue head means for applying the glue from said glue tank means to the first sheet of material, said glue head means being mounted to the glue tank means and being substantially in line with but spaced from the test path;
   air pressure means in communication with said glue tank means and said glue head means for selectively directing air pressure to said glue tank means and said glue head means and urging glue onto the first sheet of material;
   glue tank temperature control means in communication with said glue tank for measuring and controlling the temperature of the glue in the glue tank means;
   glue head temperature control means in communication with said glue head for measuring and controlling the temperature of glue in the glue head; and
   compressor means for compressing the second sheet of material against the first sheet of material after the application of the glue to the first sheet of material.

2. An apparatus as in claim 1 wherein the pressure means in communication with said glue tank means and said glue head means comprises means for measuring and controlling the pressure in said glue tank means and means for measuring and selectively controlling the pressure in said glue head means.

3. An apparatus as in claim 1 wherein said glue head means includes an adjustable and removable nozzle through which the glue flows.

4. An apparatus as in claim 1 including means mounting said glue tank means on said housing for sliding adjustable movement relative to said test path.

5. An apparatus as in claim 1 further including an adjustable speed motor mounted in said housing and in communication with said pusher means, said motor being operative to move said pusher means along said test path.

6. An apparatus as in claim 5 further including a flexible loop mounted to said pusher means and said motor, whereby said motor drives said flexible loop thereby causing the movement of said pusher means.

7. An apparatus as in claim 6 wherein said motor is operative to drive said pusher means at speeds of up to 250 feet per minute.

8. An apparatus as in claim 1 wherein said compression means includes a compression cylinder in communication with a source of air pressure, a piston slidably mounted in said compression cylinder and moveable by said air pressure, a compression bar mounted to said piston, and a vacuum source disposed adjacent said compression bar for holding the second sheet of material adjacent said compression bar.

9. An apparatus as in claim 8 further including compression control means in communication with said compression cylinder for controlling the amount of pressure directed to said compression cylinder.

10. An apparatus as in claim 9 wherein the compression control means comprises an adjustable solenoid valve in communication with said source of air pressure and said compression cylinder, said solenoid valve being operable to control the level of air pressure directed to said compression cylinder.

11. An apparatus as in claim 8 further including dwell time control means for controlling the duration of time during which the air pressure is directed to said compression cylinder.

12. An apparatus as in claim 10 further comprising vacuum control means for controlling the level of vacuum pressure in the vacuum source.

13. An apparatus as in claim 1 wherein at least one of said guides is adjustably mounted to said housing such that the distance between said guides can be varied.

14. An apparatus as in claim 1 further including switch means in communication with said air pressure means for starting or stopping the air pressure to the glue head means and the glue tank means.

15. An apparatus as in claim 14 wherein said switch means is mounted to said housing and disposed in said test path, said switch means being activatable by movement of said first sheet of material along said test path.

16. An apparatus as in claim 15 comprising a pair of spaced apart switches mounted in said test path.

17. A glue bead testing apparatus for conducting controlled tests of gluing a first sheet of material to a second sheet of material, said apparatus comprising:

a generally rigid housing including a generally planar top surface, said top surface including an elongated slot;

a pair of guides mounted to said top surface and defining a test path therebetween, said guides being disposed generally parallel to said slot and mounted on opposite sides thereof, at least one said guide being adjustably mounted to said top surface;

an adjustable speed motor mounted in said housing;

a flexible loop mounted in said housing generally parallel to said slot, said flexible loop being mounted to and driven by said motor;

at least one pusher mounted to said flexible loop and being dimensioned to extend through said slot for pushing the first sheet of material along the test path defined intermediate said guides;

a glue tank support rod mounted to said housing and being disposed generally perpendicular to said top surface;

a glue tank slidably and pivotally mounted to said glue tank support rod, said glue tank including a means for measuring and controlling the temperature of the glue therein;

a glue head mounted to said glue tank, said glue head including an adjustable and removeable nozzle disposed generally in line with the test path, said glue head further including means for measuring and controlling the temperature of the glue therein;

a compression cylinder mounted to said housing;

a piston slidably mounted in said compression cylinder, said piston including a compression bar mounted adjacent one end thereof, said compression bar being generally in line with the test path; and a vacuum tube in communication with a vacuum source and mounted to said compression bar, said vacuum tube being operative to hold the second sheet of material adjacent said compression bar.

* * * * *